United States Patent
Stopek (10) Patent No.: US 8,753,267 B2
(45) Date of Patent: Jun. 17, 2014

(54) ACCESS ASSEMBLY INSERTION DEVICE (75) Inventor: Joshua Stopek, Guilford, CT (US)

(73) Assignee: Covidien LP, Mansfield, MA (US)

( * ) Notice: Subject to any disclaimer, the term of this patent is extended or adjusted under 35 U.S.C. 154(b) by 36 days.

(21) Appl. No.: 13/311,594

(22) Filed: Dec. 6, 2011

(65) Prior Publication Data
US 2012/0190931 A1    Jul. 26, 2012

Related U.S. Application Data (60) Provisional application No. 61/435,421, filed on Jan. 24, 2011.

(51) Int. Cl.
*A61B 1/32* (2006.01)
*A61B 17/34* (2006.01)

(52) U.S. Cl.
USPC .......................................... 600/207

(58) Field of Classification Search
USPC ............... 600/204, 207, 208; 604/26, 164.03; 606/108
See application file for complete search history.

(56) References Cited

U.S. PATENT DOCUMENTS

| | | |
|---|---|---|
| 3,402,710 A | 9/1968 | Paleschuck |
| 3,495,586 A | 2/1970 | Regenbogen |
| 4,016,884 A | 4/1977 | Kwan-Gett |
| 4,112,932 A | 9/1978 | Chiulli |
| 4,183,357 A | 1/1980 | Bentley et al. |
| 4,356,826 A | 11/1982 | Kubota |
| 4,402,683 A | 9/1983 | Kopman |
| 4,653,476 A | 3/1987 | Bonnet |
| 4,737,148 A | 4/1988 | Blake |
| 4,863,430 A | 9/1989 | Klyce et al. |
| 4,863,438 A | 9/1989 | Gauderer et al. |
| 4,984,564 A | 1/1991 | Yuen |
| 5,002,557 A | 3/1991 | Hasson |
| 5,073,169 A | 12/1991 | Raiken |
| 5,082,005 A | 1/1992 | Kaldany |
| 5,122,122 A | 6/1992 | Allgood |
| 5,159,921 A | 11/1992 | Hoover |
| 5,176,697 A | 1/1993 | Hasson et al. |
| 5,183,471 A | 2/1993 | Wilk |
| 5,192,301 A | 3/1993 | Kamiya et al. |
| 5,209,754 A | 5/1993 | Ahluwalia |
| 5,217,466 A | 6/1993 | Hasson |
| 5,242,409 A | 9/1993 | Buelna |
| 5,242,415 A | 9/1993 | Kantrowitz et al. |
| 5,257,973 A | 11/1993 | Villasuso |

(Continued)

FOREIGN PATENT DOCUMENTS

| | | |
|---|---|---|
| EP | 0538060 | 4/1993 |
| EP | 0807416 | 11/1997 |

(Continued)

OTHER PUBLICATIONS

European Search Report 12 15 2132 dated Apr. 19, 2012.

*Primary Examiner* — Kevin T Truong
*Assistant Examiner* — Christian Sevilla (57) ABSTRACT

An improved access assembly is provided. The access assembly includes an inflatable port and an inflation cannula operably connected to the inflatable port to provide inflation fluid to the inflatable port. The inflatable port may be tapered in a first configuration to facilitate insertion through tissue. The inflation port defines a substantially hour-glass shape when in a second configuration to create a seal within an opening in the tissue.

6 Claims, 6 Drawing Sheets

(56) References Cited

U.S. PATENT DOCUMENTS

| | | |
|---|---|---|
| 5,257,975 A | 11/1993 | Foshee |
| 5,269,772 A | 12/1993 | Wilk |
| 5,290,249 A | 3/1994 | Foster et al. |
| 5,312,391 A | 5/1994 | Wilk |
| 5,312,417 A | 5/1994 | Wilk |
| 5,314,417 A | 5/1994 | Stephens et al. |
| 5,318,516 A | 6/1994 | Cosmescu |
| 5,330,486 A | 7/1994 | Wilk |
| 5,334,143 A | 8/1994 | Carroll |
| 5,336,169 A | 8/1994 | Divilio et al. |
| 5,336,203 A | 8/1994 | Goldhardt et al. |
| 5,345,927 A | 9/1994 | Bonutti |
| 5,360,417 A | 11/1994 | Gravener et al. |
| 5,366,478 A | 11/1994 | Brinkerhoff et al. |
| 5,375,588 A | 12/1994 | Yoon |
| 5,378,588 A | 1/1995 | Tsuchiya |
| 5,391,156 A | 2/1995 | Hildwein et al. |
| 5,394,863 A | 3/1995 | Sanford et al. |
| 5,395,367 A | 3/1995 | Wilk |
| 5,437,683 A | 8/1995 | Neumann et al. |
| 5,445,615 A | 8/1995 | Yoon |
| 5,451,222 A | 9/1995 | De Maagd et al. |
| 5,452,732 A | 9/1995 | Bircoll |
| 5,460,170 A | 10/1995 | Hammerslag |
| 5,464,409 A | 11/1995 | Mohajer |
| 5,480,410 A | 1/1996 | Cuschieri et al. |
| 5,490,843 A | 2/1996 | Hildwein et al. |
| 5,507,758 A | 4/1996 | Thomason et al. |
| 5,511,564 A | 4/1996 | Wilk |
| 5,514,133 A | 5/1996 | Golub et al. |
| 5,514,153 A | 5/1996 | Bonutti |
| 5,520,698 A | 5/1996 | Koh |
| 5,522,791 A | 6/1996 | Leyva |
| 5,524,644 A | 6/1996 | Crook |
| 5,540,648 A | 7/1996 | Yoon |
| 5,545,150 A | 8/1996 | Danks et al. |
| 5,545,179 A | 8/1996 | Williamson, IV |
| 5,556,385 A | 9/1996 | Andersen |
| 5,569,159 A | 10/1996 | Anderson et al. |
| 5,577,993 A | 11/1996 | Zhu et al. |
| 5,601,581 A | 2/1997 | Fogarty et al. |
| 5,624,399 A | 4/1997 | Ackerman |
| 5,634,911 A | 6/1997 | Hermann et al. |
| 5,634,937 A | 6/1997 | Mollenauer et al. |
| 5,643,285 A | 7/1997 | Rowden et al. |
| 5,649,550 A | 7/1997 | Crook |
| 5,651,771 A | 7/1997 | Tangherlini et al. |
| 5,653,705 A | 8/1997 | De la Torre et al. |
| 5,672,168 A | 9/1997 | De la Torre et al. |
| 5,683,378 A | 11/1997 | Christy |
| 5,685,857 A | 11/1997 | Negus et al. |
| 5,697,946 A | 12/1997 | Hopper et al. |
| 5,709,675 A | 1/1998 | Williams |
| 5,713,858 A | 2/1998 | Heruth et al. |
| 5,713,869 A | 2/1998 | Morejon |
| 5,722,962 A | 3/1998 | Garcia |
| 5,728,103 A | 3/1998 | Picha et al. |
| 5,730,748 A | 3/1998 | Fogarty et al. |
| 5,735,791 A | 4/1998 | Alexander, Jr. et al. |
| 5,741,298 A | 4/1998 | MacLeod |
| 5,782,817 A | 7/1998 | Franzel et al. |
| 5,795,290 A | 8/1998 | Bridges |
| 5,803,921 A | 9/1998 | Bonadio |
| 5,810,712 A | 9/1998 | Dunn |
| 5,813,409 A | 9/1998 | Leahy et al. |
| 5,830,191 A | 11/1998 | Hildwein et al. |
| 5,836,871 A | 11/1998 | Wallace et al. |
| 5,836,913 A | 11/1998 | Orth et al. |
| 5,840,077 A | 11/1998 | Rowden et al. |
| 5,842,971 A | 12/1998 | Yoon |
| 5,848,992 A | 12/1998 | Hart et al. |
| 5,853,417 A | 12/1998 | Fogarty et al. |
| 5,857,461 A | 1/1999 | Levitsky et al. |
| 5,865,817 A | 2/1999 | Moenning et al. |
| 5,871,474 A | 2/1999 | Hermann et al. |
| 5,876,413 A | 3/1999 | Fogarty et al. |
| 5,894,843 A | 4/1999 | Benetti et al. |
| 5,899,208 A | 5/1999 | Bonadio |
| 5,899,913 A | 5/1999 | Fogarty et al. |
| 5,904,703 A | 5/1999 | Gilson |
| 5,906,577 A | 5/1999 | Beane et al. |
| 5,914,415 A | 6/1999 | Tago |
| 5,916,198 A | 6/1999 | Dillow |
| 5,941,898 A | 8/1999 | Moenning et al. |
| 5,951,588 A | 9/1999 | Moenning |
| 5,957,913 A | 9/1999 | De la Torre et al. |
| 5,964,781 A | 10/1999 | Mollenauer et al. |
| 5,976,174 A | 11/1999 | Ruiz |
| 5,997,515 A | 12/1999 | De la Torre et al. |
| 6,017,355 A | 1/2000 | Hessel et al. |
| 6,018,094 A | 1/2000 | Fox |
| 6,024,736 A | 2/2000 | De la Torre et al. |
| 6,030,402 A | 2/2000 | Thompson et al. |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,068,639 A | 5/2000 | Fogarty et al. |
| 6,077,288 A | 6/2000 | Shimomura et al. |
| 6,086,603 A | 7/2000 | Termin et al. |
| 6,099,506 A | 8/2000 | Macoviak et al. |
| 6,110,154 A | 8/2000 | Shimomura et al. |
| 6,142,936 A | 11/2000 | Beane et al. |
| 6,156,006 A | 12/2000 | Brosens et al. |
| 6,162,196 A | 12/2000 | Hart et al. |
| 6,165,035 A * | 12/2000 | Avner ............................. 446/72 |
| 6,171,282 B1 | 1/2001 | Ragsdale |
| 6,197,002 B1 | 3/2001 | Peterson |
| 6,217,555 B1 | 4/2001 | Hart et al. |
| 6,228,063 B1 | 5/2001 | Aboul-Hosn |
| 6,234,958 B1 | 5/2001 | Snoke et al. |
| 6,238,373 B1 | 5/2001 | De la Torre et al. |
| 6,241,768 B1 | 6/2001 | Agarwal et al. |
| 6,251,119 B1 | 6/2001 | Addis |
| 6,254,534 B1 | 7/2001 | Butler et al. |
| 6,264,604 B1 | 7/2001 | Kieturakis et al. |
| 6,276,661 B1 | 8/2001 | Laird |
| 6,293,952 B1 | 9/2001 | Brosens et al. |
| 6,315,770 B1 | 11/2001 | De la Torre et al. |
| 6,319,246 B1 | 11/2001 | De la Torre et al. |
| 6,328,720 B1 | 12/2001 | McNally et al. |
| 6,371,968 B1 | 4/2002 | Kogasaka et al. |
| 6,382,211 B1 | 5/2002 | Crook |
| 6,423,036 B1 | 7/2002 | Van Huizen |
| 6,440,061 B1 | 8/2002 | Wenner et al. |
| 6,440,063 B1 | 8/2002 | Beane et al. |
| 6,443,957 B1 | 9/2002 | Addis |
| 6,447,489 B1 | 9/2002 | Peterson |
| 6,450,983 B1 | 9/2002 | Rambo |
| 6,454,783 B1 | 9/2002 | Piskun |
| 6,464,686 B1 | 10/2002 | O'Hara et al. |
| 6,468,292 B1 | 10/2002 | Mollenauer et al. |
| 6,485,410 B1 | 11/2002 | Loy |
| 6,488,620 B1 | 12/2002 | Segermark |
| 6,488,692 B1 | 12/2002 | Spence et al. |
| 6,524,283 B1 | 2/2003 | Hopper et al. |
| 6,527,787 B1 | 3/2003 | Fogarty et al. |
| 6,544,210 B1 | 4/2003 | Trudel et al. |
| 6,551,270 B1 | 4/2003 | Bimbo et al. |
| 6,558,371 B2 | 5/2003 | Dorn |
| 6,562,022 B2 | 5/2003 | Hoste et al. |
| 6,572,631 B1 | 6/2003 | McCartney |
| 6,578,577 B2 | 6/2003 | Bonadio et al. |
| 6,582,364 B2 | 6/2003 | Butler et al. |
| 6,589,167 B1 | 7/2003 | Shimomura et al. |
| 6,589,316 B1 | 7/2003 | Schultz et al. |
| 6,592,543 B1 | 7/2003 | Wortrich et al. |
| 6,613,952 B2 | 9/2003 | Rambo |
| 6,623,426 B2 | 9/2003 | Bonadio et al. |
| 6,656,013 B1 | 12/2003 | Wang |
| 6,669,674 B1 | 12/2003 | Macoviak et al. |
| 6,676,639 B1 | 1/2004 | Ternstrom |
| 6,706,050 B1 | 3/2004 | Giannadakis |

(56) References Cited

U.S. PATENT DOCUMENTS

| | | |
|---|---|---|
| 6,716,201 B2 | 4/2004 | Blanco |
| 6,723,044 B2 | 4/2004 | Pulford et al. |
| 6,723,088 B2 | 4/2004 | Gaskill, III et al. |
| 6,725,080 B2 | 4/2004 | Melkent et al. |
| 6,800,084 B2 | 10/2004 | Davison et al. |
| 6,808,520 B1 | 10/2004 | Fourkas et al. |
| 6,811,546 B1 | 11/2004 | Callas et al. |
| 6,814,078 B2 | 11/2004 | Crook |
| 6,830,578 B2 | 12/2004 | O'Heeron et al. |
| 6,837,893 B2 | 1/2005 | Miller |
| 6,840,946 B2 | 1/2005 | Fogarty et al. |
| 6,840,951 B2 | 1/2005 | De La Torre et al. |
| 6,846,287 B2 | 1/2005 | Bonadio et al. |
| 6,863,674 B2 | 3/2005 | Kasahara et al. |
| 6,878,110 B2 | 4/2005 | Yang et al. |
| 6,884,253 B1 | 4/2005 | McFarlane |
| 6,890,295 B2 | 5/2005 | Michels et al. |
| 6,913,609 B2 | 7/2005 | Yencho et al. |
| 6,916,310 B2 | 7/2005 | Sommerich |
| 6,916,331 B2 | 7/2005 | Mollenauer et al. |
| 6,929,637 B2 | 8/2005 | Gonzalez et al. |
| 6,939,296 B2 | 9/2005 | Ewers et al. |
| 6,942,633 B2 | 9/2005 | Odland |
| 6,945,932 B1 | 9/2005 | Caldwell et al. |
| 6,958,037 B2 | 10/2005 | Ewers et al. |
| 6,972,026 B1 | 12/2005 | Caldwell et al. |
| 6,986,752 B2 | 1/2006 | McGuckin, Jr. et al. |
| 6,991,602 B2 | 1/2006 | Nakazawa et al. |
| 6,997,909 B2 | 2/2006 | Goldberg |
| 7,001,397 B2 | 2/2006 | Davison et al. |
| 7,008,377 B2 | 3/2006 | Beane et al. |
| 7,011,645 B2 | 3/2006 | McGuckin, Jr. et al. |
| 7,014,628 B2 | 3/2006 | Bousquet |
| 7,033,319 B2 | 4/2006 | Pulford et al. |
| 7,052,454 B2 | 5/2006 | Taylor |
| 7,056,321 B2 | 6/2006 | Pagliuca et al. |
| 7,077,852 B2 | 7/2006 | Fogarty et al. |
| 7,081,089 B2 | 7/2006 | Bonadio et al. |
| 7,083,626 B2 | 8/2006 | Hart et al. |
| 7,100,614 B2 | 9/2006 | Stevens et al. |
| 7,101,353 B2 | 9/2006 | Lui et al. |
| 7,104,981 B2 | 9/2006 | Elkins et al. |
| 7,153,261 B2 | 12/2006 | Wenchell |
| 7,160,309 B2 | 1/2007 | Voss |
| 7,163,510 B2 | 1/2007 | Kahle et al. |
| 7,192,436 B2 | 3/2007 | Sing et al. |
| 7,195,590 B2 | 3/2007 | Butler et al. |
| 7,201,725 B1 | 4/2007 | Cragg et al. |
| 7,214,185 B1 | 5/2007 | Rosney et al. |
| 7,217,277 B2 | 5/2007 | Parihar et al. |
| 7,223,257 B2 | 5/2007 | Shubayev et al. |
| 7,223,278 B2 | 5/2007 | Davison et al. |
| 7,235,064 B2 | 6/2007 | Hopper et al. |
| 7,235,084 B2 | 6/2007 | Skakoon et al. |
| 7,238,154 B2 | 7/2007 | Ewers et al. |
| 7,258,712 B2 | 8/2007 | Schultz et al. |
| 7,276,075 B1 | 10/2007 | Callas et al. |
| 7,294,103 B2 | 11/2007 | Bertolero et al. |
| 7,300,399 B2 | 11/2007 | Bonadio et al. |
| 7,316,699 B2 | 1/2008 | McFarlane |
| 7,331,940 B2 | 2/2008 | Sommerich |
| 7,344,547 B2 | 3/2008 | Piskun |
| 7,377,898 B2 | 5/2008 | Ewers et al. |
| 7,390,322 B2 | 6/2008 | McGuckin, Jr. et al. |
| 7,393,322 B2 | 7/2008 | Wenchell |
| 7,412,977 B2 | 8/2008 | Fields et al. |
| 7,440,661 B2 | 10/2008 | Kobayashi |
| 7,445,597 B2 | 11/2008 | Butler et al. |
| 7,452,363 B2 | 11/2008 | Ortiz |
| 7,473,221 B2 | 1/2009 | Ewers et al. |
| 7,481,765 B2 | 1/2009 | Ewers et al. |
| 7,493,703 B2 | 2/2009 | Kim et al. |
| 7,513,361 B1 | 4/2009 | Mills, Jr. |
| 7,513,461 B2 | 4/2009 | Reutenauer et al. |
| 7,520,876 B2 | 4/2009 | Ressemann et al. |
| 7,537,564 B2 | 5/2009 | Bonadio et al. |
| 7,540,839 B2 | 6/2009 | Butler et al. |
| 7,559,893 B2 | 7/2009 | Bonadio et al. |
| 7,608,082 B2 | 10/2009 | Cuevas et al. |
| 7,625,361 B2 | 12/2009 | Suzuki et al. |
| 7,645,232 B2 | 1/2010 | Shluzas |
| 7,650,887 B2 | 1/2010 | Nguyen et al. |
| 7,704,207 B2 | 4/2010 | Albrecht et al. |
| 7,717,846 B2 | 5/2010 | Zirps et al. |
| 7,717,847 B2 | 5/2010 | Smith |
| 7,721,742 B2 | 5/2010 | Kalloo et al. |
| 7,727,146 B2 | 6/2010 | Albrecht et al. |
| 7,730,629 B2 | 6/2010 | Kim |
| 7,736,306 B2 | 6/2010 | Brustad et al. |
| 7,753,901 B2 | 7/2010 | Piskun et al. |
| 7,758,500 B2 | 7/2010 | Boyd et al. |
| 7,766,824 B2 | 8/2010 | Jensen et al. |
| 7,787,963 B2 | 8/2010 | Geistert et al. |
| 7,798,998 B2 | 9/2010 | Thompson et al. |
| 7,811,251 B2 | 10/2010 | Wenchell et al. |
| 7,815,567 B2 | 10/2010 | Albrecht et al. |
| 7,837,612 B2 | 11/2010 | Gill et al. |
| 7,846,123 B2 | 12/2010 | Vassiliades et al. |
| 7,850,600 B1 * | 12/2010 | Piskun ............................ 600/114 |
| 7,850,667 B2 | 12/2010 | Gresham |
| 7,867,164 B2 | 1/2011 | Butler et al. |
| 7,896,889 B2 | 3/2011 | Mazzocchi et al. |
| 7,905,829 B2 | 3/2011 | Nishimura et al. |
| 7,909,760 B2 | 3/2011 | Albrecht et al. |
| 7,951,076 B2 | 5/2011 | Hart et al. |
| 7,955,257 B2 | 6/2011 | Frasier et al. |
| 7,955,313 B2 | 6/2011 | Boismier |
| 7,998,068 B2 | 8/2011 | Bonadio et al. |
| 8,021,296 B2 | 9/2011 | Bonadio et al. |
| 8,025,670 B2 | 9/2011 | Sharp et al. |
| 8,038,652 B2 | 10/2011 | Morrison et al. |
| 8,066,673 B2 | 11/2011 | Hart et al. |
| 8,079,986 B2 | 12/2011 | Taylor et al. |
| 8,105,234 B2 | 1/2012 | Ewers et al. |
| 8,157,786 B2 | 4/2012 | Miller et al. |
| 8,157,817 B2 | 4/2012 | Bonadio et al. |
| 8,187,177 B2 | 5/2012 | Kahle et al. |
| 8,187,178 B2 | 5/2012 | Bonadio et al. |
| 2001/0037053 A1 | 11/2001 | Bonadio et al. |
| 2002/0055714 A1 | 5/2002 | Rothschild |
| 2003/0014076 A1 | 1/2003 | Mollenauer et al. |
| 2003/0093104 A1 | 5/2003 | Bonner et al. |
| 2003/0236549 A1 | 12/2003 | Bonadio et al. |
| 2004/0059297 A1 | 3/2004 | Racenet et al. |
| 2004/0092795 A1 | 5/2004 | Bonadio et al. |
| 2004/0102804 A1 | 5/2004 | Chin |
| 2004/0111061 A1 | 6/2004 | Curran |
| 2004/0138529 A1 | 7/2004 | Wiltshire et al. |
| 2004/0204734 A1 | 10/2004 | Wagner et al. |
| 2004/0267096 A1 | 12/2004 | Caldwell et al. |
| 2005/0020884 A1 | 1/2005 | Hart et al. |
| 2005/0070935 A1 | 3/2005 | Ortiz |
| 2005/0096695 A1 | 5/2005 | Olich |
| 2005/0137459 A1 | 6/2005 | Chin et al. |
| 2005/0148823 A1 | 7/2005 | Vaugh et al. |
| 2005/0159711 A1 * | 7/2005 | Kathrani et al. .............. 604/264 |
| 2005/0192483 A1 | 9/2005 | Bonadio et al. |
| 2005/0203346 A1 | 9/2005 | Bonadio et al. |
| 2005/0245876 A1 | 11/2005 | Khosravi et al. |
| 2005/0251092 A1 | 11/2005 | Howell et al. |
| 2005/0277946 A1 | 12/2005 | Greenhalgh |
| 2006/0071432 A1 | 4/2006 | Staudner |
| 2006/0129165 A1 | 6/2006 | Edoga et al. |
| 2006/0149137 A1 | 7/2006 | Pingleton et al. |
| 2006/0149306 A1 | 7/2006 | Hart et al. |
| 2006/0161049 A1 | 7/2006 | Beane et al. |
| 2006/0161050 A1 | 7/2006 | Butler et al. |
| 2006/0212063 A1 | 9/2006 | Wilk |
| 2006/0224161 A1 | 10/2006 | Bhattacharyya |
| 2006/0241651 A1 | 10/2006 | Wilk |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |

(56) References Cited

U.S. PATENT DOCUMENTS

| | | |
|---|---|---|
| 2006/0247673 A1 | 11/2006 | Voegele et al. |
| 2006/0247678 A1 | 11/2006 | Weisenburgh, II et al. |
| 2006/0270911 A1 | 11/2006 | Voegele et al. |
| 2007/0118175 A1 | 5/2007 | Butler et al. |
| 2007/0203398 A1 | 8/2007 | Bonadio et al. |
| 2007/0208312 A1 | 9/2007 | Norton et al. |
| 2007/0255231 A1* | 11/2007 | Gross et al. ............ 604/272 |
| 2007/0270654 A1 | 11/2007 | Pignato et al. |
| 2007/0270882 A1 | 11/2007 | Hjelle et al. |
| 2008/0027476 A1 | 1/2008 | Piskun |
| 2008/0048011 A1 | 2/2008 | Weller |
| 2008/0097162 A1 | 4/2008 | Bonadio et al. |
| 2008/0097332 A1 | 4/2008 | Greenhalgh et al. |
| 2008/0161826 A1 | 7/2008 | Guiraudon |
| 2008/0194973 A1 | 8/2008 | Imam |
| 2008/0200767 A1 | 8/2008 | Ewers et al. |
| 2008/0255519 A1 | 10/2008 | Piskun et al. |
| 2008/0319261 A1 | 12/2008 | Lucini |
| 2009/0012477 A1 | 1/2009 | Norton et al. |
| 2009/0036738 A1 | 2/2009 | Cuschieri et al. |
| 2009/0043167 A1* | 2/2009 | Leiner ............ 600/156 |
| 2009/0093752 A1 | 4/2009 | Richard et al. |
| 2009/0093850 A1 | 4/2009 | Richard |
| 2009/0105635 A1 | 4/2009 | Bettuchi et al. |
| 2009/0131751 A1 | 5/2009 | Spivey et al. |
| 2009/0182279 A1 | 7/2009 | Wenchell et al. |
| 2009/0182288 A1 | 7/2009 | Spenciner |
| 2009/0187079 A1 | 7/2009 | Albrecht et al. |
| 2009/0204067 A1 | 8/2009 | Abu-Halawa |
| 2009/0227843 A1 | 9/2009 | Smith et al. |
| 2009/0326330 A1 | 12/2009 | Bonadio et al. |
| 2009/0326332 A1 | 12/2009 | Carter |
| 2010/0063452 A1 | 3/2010 | Edelman et al. |
| 2010/0100043 A1 | 4/2010 | Racenet |
| 2010/0240960 A1 | 9/2010 | Richard |
| 2010/0249523 A1 | 9/2010 | Spiegal et al. |
| 2010/0249524 A1 | 9/2010 | Ransden et al. |
| 2010/0286484 A1 | 11/2010 | Stellon et al. |
| 2010/0286506 A1 | 11/2010 | Ransden et al. |
| 2010/0298646 A1 | 11/2010 | Stellon et al. |
| 2011/0009704 A1 | 1/2011 | Marczyk et al. |
| 2011/0021877 A1 | 1/2011 | Fortier et al. |
| 2011/0028891 A1 | 2/2011 | Okoniewski |
| 2011/0034778 A1 | 2/2011 | Kleyman |
| 2011/0054257 A1 | 3/2011 | Stopek |
| 2011/0054258 A1 | 3/2011 | O'Keefe et al. |
| 2011/0082341 A1 | 4/2011 | Kleyman et al. |
| 2011/0082343 A1 | 4/2011 | Okoniewski |
| 2011/0082346 A1 | 4/2011 | Stopek |
| 2011/0118553 A1 | 5/2011 | Stopek |
| 2011/0124968 A1 | 5/2011 | Kleyman |
| 2011/0124969 A1 | 5/2011 | Stopek |
| 2011/0124970 A1 | 5/2011 | Kleyman |
| 2011/0125186 A1 | 5/2011 | Fowler et al. |
| 2011/0166423 A1 | 7/2011 | Farascioni et al. |

FOREIGN PATENT DOCUMENTS

| | | |
|---|---|---|
| EP | 1188415 | 3/2002 |
| EP | 1312318 | 5/2003 |
| EP | 0950376 | 5/2006 |
| EP | 1774918 | 4/2007 |
| EP | 1932485 | 6/2008 |
| EP | 2044889 | 4/2009 |
| EP | 2095781 | 9/2009 |
| EP | 2229900 | 9/2010 |
| EP | 2238924 | 10/2010 |
| EP | 2238925 | 10/2010 |
| EP | 2248478 | 11/2010 |
| EP | 2253283 | 11/2010 |
| EP | 2272450 | 1/2011 |
| EP | 2277464 | 1/2011 |
| EP | 2292165 | 3/2011 |
| WO | WO 93/14801 | 8/1993 |
| WO | WO94/04067 | 3/1994 |
| WO | WO96/36283 | 11/1996 |
| WO | WO97/33520 | 9/1997 |
| WO | WO97/42889 | 11/1997 |
| WO | WO99/16368 | 4/1999 |
| WO | WO99/22804 | 5/1999 |
| WO | WO00/32116 | 6/2000 |
| WO | WO00/32120 | 6/2000 |
| WO | WO01/08581 | 2/2001 |
| WO | WO01/49363 | 7/2001 |
| WO | WO02/07611 | 1/2002 |
| WO | WO03/034908 | 5/2003 |
| WO | WO03/071926 | 9/2003 |
| WO | WO2004/043275 | 5/2004 |
| WO | WO2004/054456 | 7/2004 |
| WO | WO2004/075741 | 9/2004 |
| WO | WO2004/075930 | 9/2004 |
| WO | WO2006/019723 | 2/2006 |
| WO | WO2006/100658 | 9/2006 |
| WO | WO2006/110733 | 10/2006 |
| WO | WO2007/095703 | 8/2007 |
| WO | WO2007/143200 | 12/2007 |
| WO | WO2008/015566 | 2/2008 |
| WO | WO2008/042005 | 4/2008 |
| WO | WO2008/077080 | 6/2008 |
| WO | WO2008/093313 | 8/2008 |
| WO | WO2008/103151 | 8/2008 |
| WO | WO2008/121294 | 10/2008 |
| WO | WO2009/036343 | 3/2009 |

* cited by examiner

ACCESS ASSEMBLY INSERTION DEVICE

CROSS REFERENCE TO RELATED APPLICATION

The present application claims the benefit of and priority to U.S. Provisional Application Ser. No. 61/435,421 filed on Jan. 24, 2011, the entire contents of which are incorporated herein by reference.

BACKGROUND

1. Technical Field

The present disclosure relates to apparatus and method for accessing a body cavity. More particularly, the present disclosure relates to an inflatable assembly for accessing a body cavity.

2. Background of Related Art

Access assemblies configured for reception through an incision into an abdominal cavity are known, as are methods of inserting the access assemblies therethrough. Traditional access assemblies include a rigid cannula that is received through the tissue of the body wall into the body cavity. Endoscopic, laparoscopic and other suitable instruments may then be directed through a housing on the proximal end of the cannula to access the body cavity in a sealing manner.

Compressible assemblies configured for accessing a body cavity and permitting reception of instruments therethrough in sealing manner are also known. Such compressible assemblies are composed of silicone, thermoplastic elastomers (TPE), rubber, foam, gel and other compressible materials and are configured to be compressed to facilitate insertion into an incision. Typically, such assemblies are deformed by a surgeon using his/her fingers or with the assistance of a grasping device, i.e., forceps. Compression of the assembly reduces the profile of the assembly, thereby facilitating reception of the assembly into the incision. Upon release of the compressive force, the compressed assembly returns to an uncompressed configuration. In the uncompressed configuration, the access assembly seals the incision into the body cavity. The assembly may have one or more access ports for receiving instruments therethrough and may optionally be configured for connection with a source of insufflation gas.

Excessive handling of the compressible access assemblies during placement of the assembly through an incision may compromise or otherwise negatively effect the integrity of the assembly. For example, any coating on the assembly may be rubbed off during handling, or excessive force, oversized/undersized fingers and/or sharp grasping instruments may tear the material comprising the assembly.

Therefore, it would be beneficial to have an access assembly configured to be inserted through tissue without excessive handling and/or without the need for an insertion device.

SUMMARY

Accordingly, an improved access assembly is provided. The access assembly includes an inflatable port and an inflation cannula operably connected to the inflatable port to provide inflation fluid to the inflatable port. The inflatable port may be tapered in a first configuration to facilitate insertion through tissue. The inflation port defines a substantially hour-glass shape when in a second configuration to create a seal within an opening in the tissue.

The inflatable port may include an upper rim configured to be received external of the tissue and a lower rim configured to be received within a body cavity. In one embodiment, the inflation cannula includes a sharpened distal tip. The access assembly may further include a sleeve to maintain the inflatable port in the tapered configuration. A proximal end of the inflation cannula may be configured for operable connection with a source of inflation fluid. The inflatable port may be one of molded, extruded and sewn. In one embodiment, the inflatable port is twisted about the inflation cannula when in the first configuration.

Also provided is a method of accessing a body cavity. The method includes the step of providing an access assembly including an inflatable port and a inflation cannula, wherein the inflatable port include a tapered configuration to facilitate reception through tissue and an hour-glass configuration to maintain the assembly within tissue, inserting the tapered access assembly through tissue, inflating the inflatable access assembly, and performing a procedure through the access assembly.

The method may further include the steps of deflating the inflatable port and removing the port from the tissue. Additionally, the method may include the step of creating an incision in the tissue and connecting the inflation cannula with a source of inflation fluid. The inflation cannula may include a piercing tip.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user. While the use of the access assembly is often described herein as engaging an incision, it should be recognized that this is merely exemplary and is not intended to limit the use of the assembly in any way, but rather it should be recognized that the present invention is intended to be useable in all instances in situations in which the access assembly engages an incision, a naturally occurring orifice, or any other suitable opening.

Referring initially to FIGS. 1-5, an assembly for access a body cavity is shown generally as access assembly 100. In a first or tapered configuration (FIGS. 1 and 2), access assembly 100 is configured to be inserted through an incision or other opening in tissue without excessive handling or manipulation of assembly 100 and without a separate insertion device. Alternatively, and as will be discussed in further detail below, access assembly 100 may include a sharpened or bladed tip configured for creating the opening in the tissue for reception of access assembly 100 therethrough. In a second or deflated configuration (FIG. 3), access assembly 100 is configured to be withdrawn from an opening following completion of a surgical procedure. In a third or inflated configuration (FIG. 4), access assembly 100 is configured to selectively seal an opening through tissue into a body cavity. In the third configuration, access assembly 100 is further configured to receive one or more instruments therethrough in a sealing manner.

With reference still to FIGS. 1-5, access assembly 100 includes an inflatable port 110 and an inflation cannula 130. Inflatable port 110 is constructed of plastic, polymer, fabric or other suitable material. Inflatable port 110 may be molded, extruded, sewn or formed in any other suitable manner. Inflation cannula 130 is formed of plastic, polymer, metal or any other suitable material. In one embodiment, and as shown, inflation cannula 130 is securely affixed to inflation port 110 by adhesive, bonding, welding or other suitable means. In an alternative embodiment, inflation cannula 130 may be configured for selective engagement with inflatable port 110. In this manner, inflation cannula 130 does not interfere with manipulation of instruments inserted through inflatable port 110.

Inflation cannula 130 includes one or more openings 132 formed along a length thereof in communication with a cavity 111 (FIG. 5) within inflatable port 110. A proximal end 130a of inflation cannula 130 is configured for operable connection to a source of inflation fluid 50 (FIG. 6). Proximal end 130a of cannula 130 may extend beyond a proximal end 116 of inflatable port 110, as shown, and may include a connection assembly 134 configured to operably connect with a inflation tube 52 (FIG. 6). Alternatively, proximal end 130a of cannula 130 may be recessed within inflatable port 110. In this manner, proximal end 130a of cannula 130 will not obstruct manipulation of an instrument inserted through port 110. In another embodiment, proximal end 130a of cannula 130 is integrally formed with inflation tube 52. As will be discussed in further detail below, a distal end 130b of inflation cannula 130 may be pointed, sharpened or otherwise configured to facilitate insertion of access assembly 100 through tissue.

Figure 1:
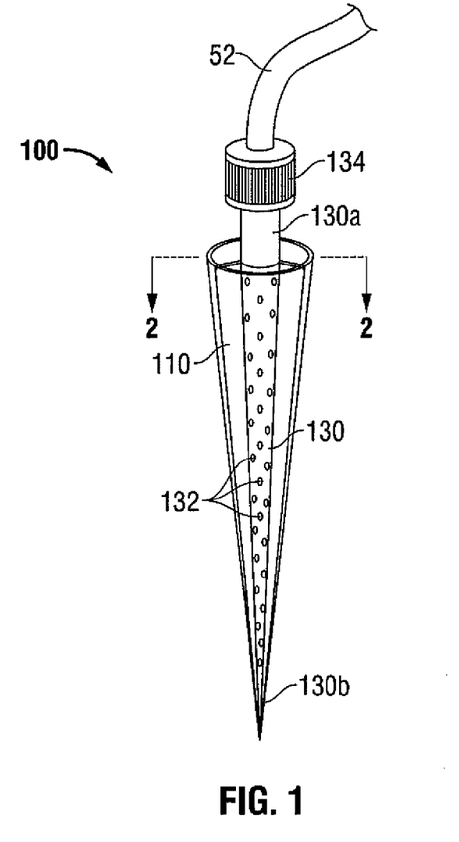
FIG. 1 is a perspective view of an embodiment of an access assembly according to an aspect of the present disclosure, in a first or tapered configuration.
Figure 2:
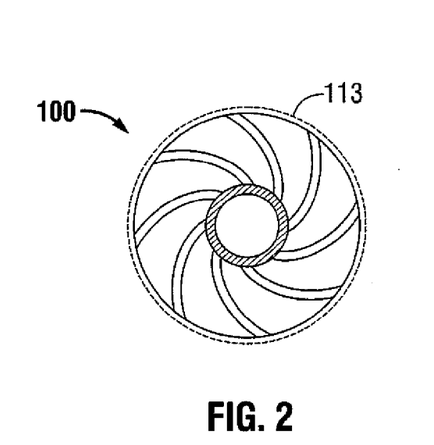
FIG. 2 is a partial cross-sectional top view of the access assembly of FIG. 1, taken along line 1-1.

With particular reference now to FIGS. 1 and 2, in the first or tapered configuration, access assembly 100 forms a substantially tapered member configured to be inserted through an opening formed in tissue. Access assembly 100 may be provided to a surgeon in the first configuration or instead are provided in the second configuration, and thus require forming into the tapered configuration prior to insertion through tissue. Inflation cannula 130 extends at least partially along the length of inflatable port 110 and may include a tapered configuration to facilitate the shaping of inflatable port 110 thereabout and/or to facilitate insertion of access assembly 100. It is envisioned that inflation cannula 130 may extend beyond a distal end of inflation port 110 to further facilitate insertion of access assembly 100 through tissue.

With reference still to FIGS. 1 and 2, in one embodiment, and as shown, inflatable port 110 is twisted about inflation cannula 130 to achieve the tapered configuration. Inflatable port 110 may be maintained in the tapered configuration using a temporary adhesive, a dissolvable coating, a tear-away sleeve 113 (FIG. 2, shown in phantom) or any other suitable means. In an alternate embodiment, a shrink-wrap sleeve or tube may be used to achieve the tapered configuration of access assembly 100. As will be described in further detail below, either upon receipt within an opening formed in tissue or upon the start of inflation of inflatable port 110, the adhesive, coating, sleeve 113 or other material maintaining inflatable port 110 in the tapered configuration dissolves, tears or otherwise releases inflatable port 110 from the tapered configuration, thereby permitting inflation of inflatable port 110.

Figure 3:
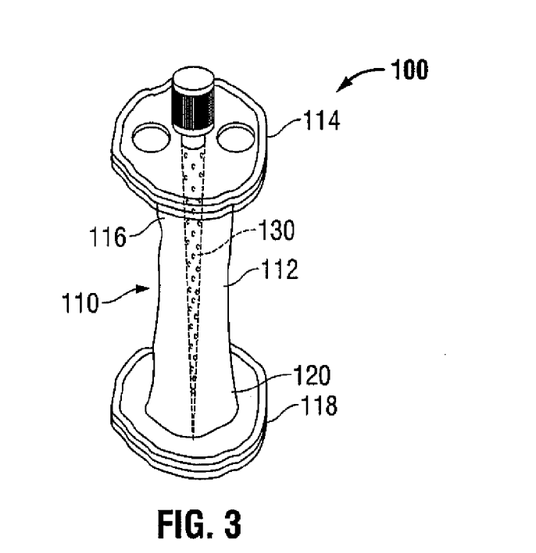
FIG. 3 is a perspective view of the access assembly of FIGS. 1 and 2, in a second or deflated configuration.

With reference now to FIG. 3, access assembly 100 is shown in a second or deflated configuration. During use, access assembly 100 is in the second or deflated configuration prior to inflation of inflatable port 110 and upon completion of a procedure therethrough. In the second or deflated configuration, inflatable port 110 defines a member having a substantially similar shape to that of the inflated inflatable port 110, as described below. In the second or deflated configuration, access assembly 110 may be adjusted within an opening in tissue and/or may be removed therefrom.

Figure 4:
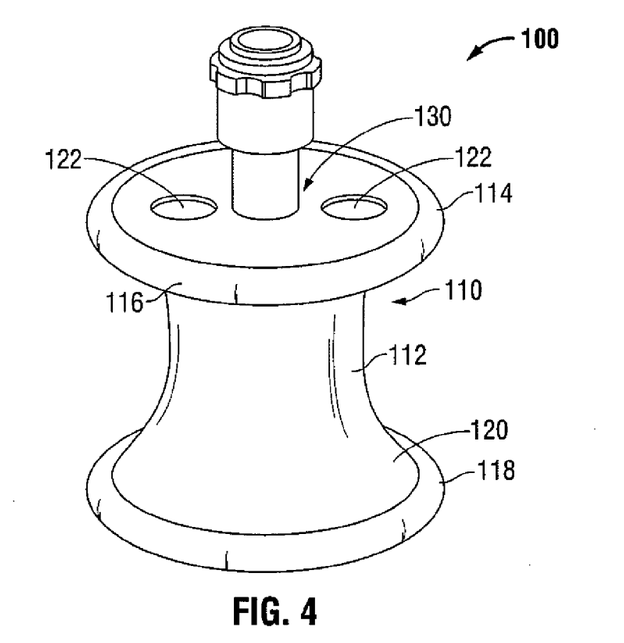
FIG. 4 is a perspective view of the access assembly of FIGS. 1-3, in a third or inflated configuration.

With particular reference now to FIG. 4, access assembly 100 is shown in the third or inflated configuration. In the third or inflated configuration, inflatable port 110 creates a seal within an opening to prevent the escape of insufflation gas therethough. Inflatable port 110 may be inflated with any suitable fluid, including an insufflation gas or water. Inflatable port 110 defines a substantially hourglass shape when viewed from the side. Inflatable port 110 includes a central portion 112 having an upper rim 114 located at a proximal end 116 of central portion 112 and a lower rim 118 located at a distal end 120 of central portion 112. Upper rim 114 and lower rim 118 aid in minimizing movement of access port 110 longitudinally through an opening. Central portion 112 is of a length sufficient that upper rim 114 is maintained external the body while lower rim 118 is received within the abdominal cavity.

Figure 5:
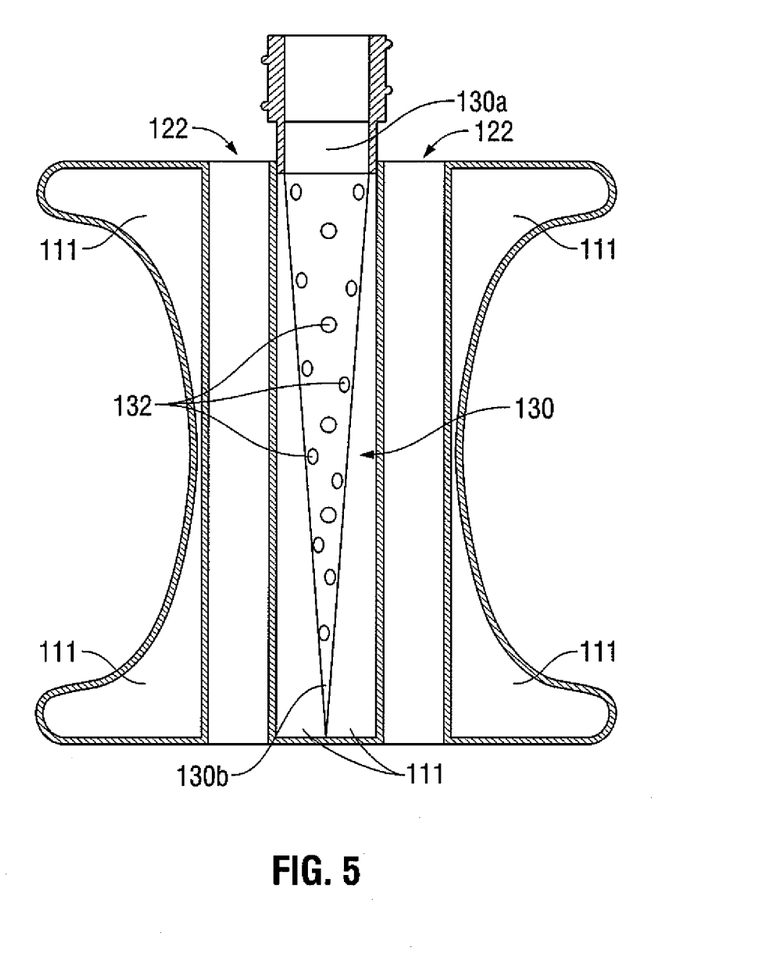
FIG. 5 is a cross-section side view of the access assembly of FIGS. 1-4, in the third or inflated configurations.
Figure 6:
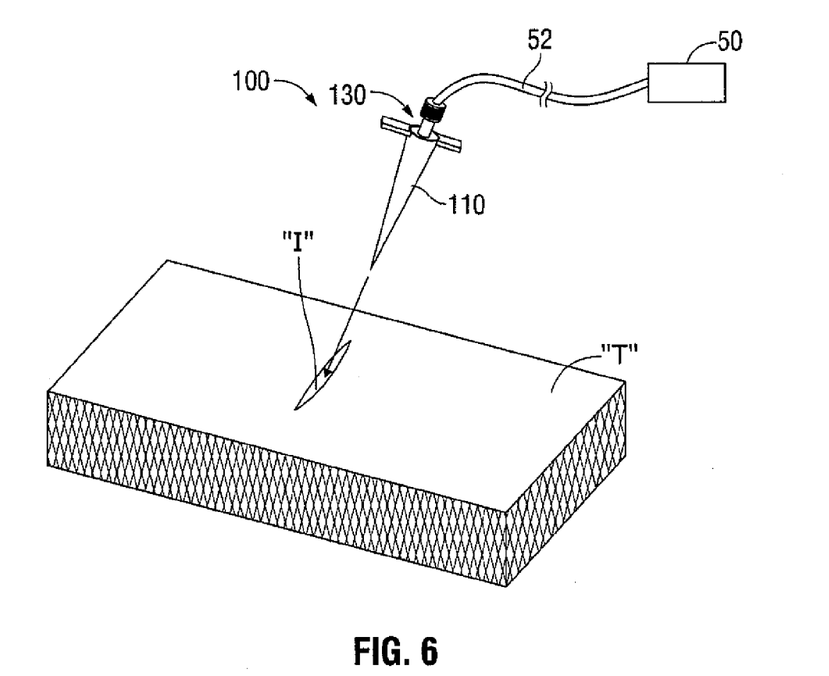
FIGS. 6-10 illustrate sequential steps for providing access to a body cavity using the access assembly of FIGS. 1-5.
Figure 7:
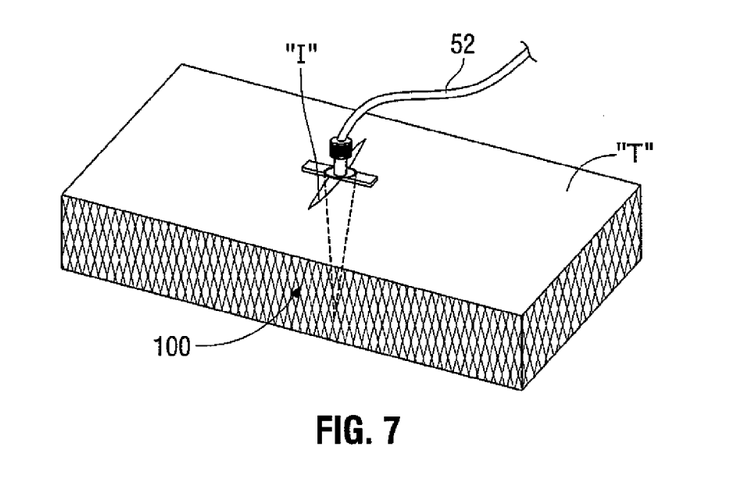

With specific reference now to FIG. 5, a plurality of lumen 122 extend through port 110 along a longitudinal axis and are configured to receive surgical instruments therethrough in a sealing manner. Although shown including two lumen 122, it is envisioned that access assembly 100 may include one or more lumen 122. Although shown including a centrally located inflation cannula 130 and radially spaced lumen 122, it is envisioned that the arrangement of inflation cannula 130 and the one or more lumen 122 may be modified to better suit an application or procedure. Lumen 122 may be configured to directly seal one or more instruments inserted therethrough. Alternatively, each of lumen 122 may include one or more valve members (not shown) for receiving an instrument therethrough in a sealing manner. Additionally, the one or more valve members may seal lumen 122 in the absence of an instrument received therethrough. In yet another embodiment, lumen 122 are configured to receive cannula assemblies (not shown) therein. Each of the cannula assemblies may include a valve member for receiving an instrument in a sealing manner.

With reference now to FIGS. 6-10, the use of access assembly 100 will be described. Whether inflatable port 110 is provided to a surgeon in the tapered configuration of FIGS. 1 and 2, or in the non-tapered configuration of FIGS. 3 and 4, and thereby requires further manipulation by a surgeon to form the tapered configuration, access assembly 100 is initially received through tissue "T" with inflatable port 110 in the tapered configuration to facilitate insertion thereof. As discussed above, access assembly 100 may be inserted through an incision "I" in tissue "T" that has been created by an incision. Alternatively, inflation cannula 130 of access assembly 100 may include a piercing or cutting tip to create incision "I" as access assembly 100 engages tissue "T". In yet another procedure, access assembly 100 is inserted through a natural opening, i.e., anus or vagina. As discussed above, access assembly 100 may be operably connected to a source of insuflation gas 50 via tube 52 prior to, during, or upon insertion of access assembly 100 within incision "I".

Once received through tissue "T" (FIG. 7), either upon receipt within tissue "T" or upon the start of inflation of inflatable port 110, the adhesive, coating, sleeve or other material maintaining inflatable port 110 in the tapered configuration dissolves, tears or otherwise releases inflatable port 110 from the tapered configuration, thereby permitting inflation of inflatable port 110.

Figure 8:
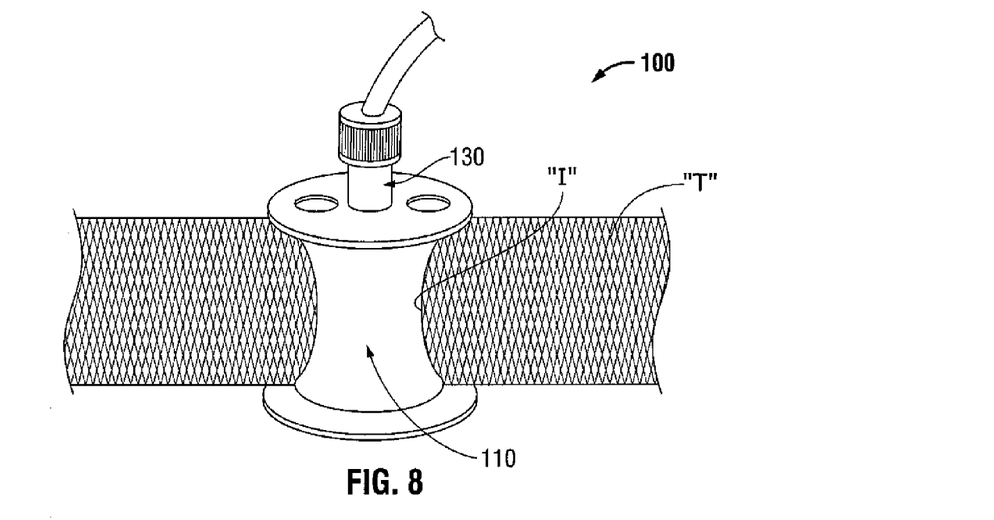
Figure 9:
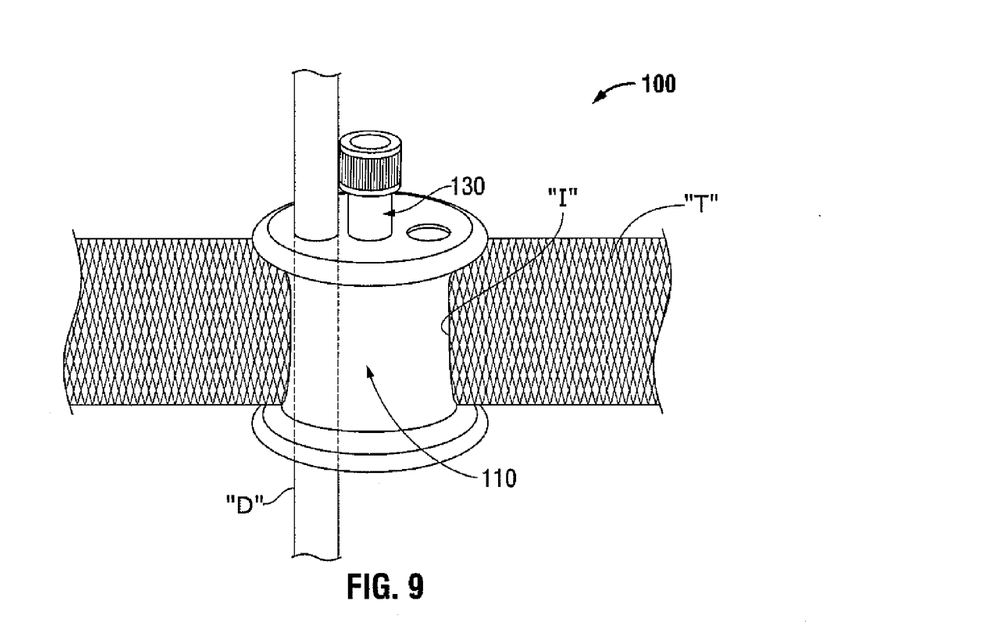

Turning now to FIGS. 8 and 9, inflatable port 110 is inflated within tissue "T" to seal incision "I". Inflatable port 110 operates as a conventional access assembly, capable of receiving one or more instruments or devices "D" through lumen 122. Tube 52 may be disconnected from proximal end 130a of cannula 130 to prevent interference therewith as instruments "D" are manipulated through access assembly 100.

Figure 10:
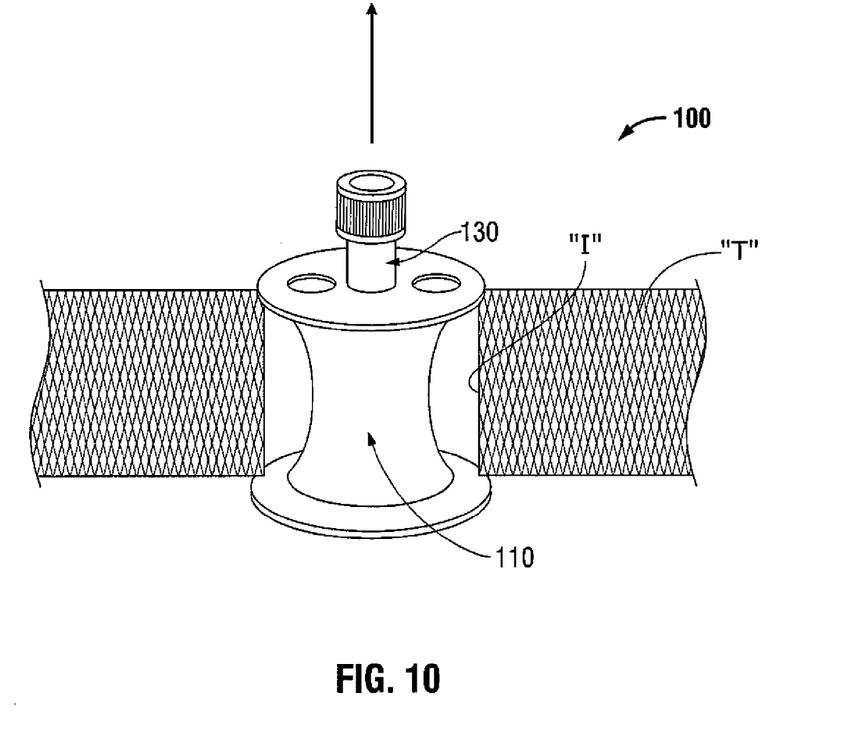

With reference now to FIG. 10, once a procedure is completed, inflatable port 110 is deflated either by opening a valve (not shown) or piercing inflatable port 110 to return inflatable port 110 to the deflated configuration to permit removal from within incision "I". In the deflated configuration, inflatable port 110 may be easily removed from tissue "T". Incision "I" may then be closed in a conventional manner.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

The invention claimed is:

1. A surgical access system comprising:
   an inflatable port having a proximal portion, a body portion, and a distal portion, the inflatable port transitionable between a first state and a second state, the first state defined by the proximal portion having a diameter greater than a diameter of the body portion and a diameter of the distal portion such that the inflatable port has a tapered configuration to facilitate insertion through tissue, the second state defined by the diameter of the proximal portion and the diameter of the distal portion both being greater than the diameter of the body portion; and
   an inflation cannula having a tapered distal tip, the inflation cannula disposed within the inflatable port for supplying fluid to the inflatable port such that when the inflatable port is wrapped around the inflation cannula in the first state, the inflatable port is in the tapered configuration and when fluid is supplied to the inflatable port, the inflatable port transitions to the second state.

2. The access assembly of claim 1, wherein, in the second state, the proximal portion of the inflatable port includes an upper rim configured to be positioned external of tissue.

3. The access assembly of claim 1, wherein, in the second state, the proximal portion of the inflatable port includes a lower rim configured to be received within a body cavity.

4. The access assembly of claim 1, further including a sleeve to maintain the inflatable port in the tapered configuration when in the first state.

5. The access assembly of claim 1, wherein a proximal end of the inflation cannula is connectable to a source of inflation fluid.

6. The access assembly of claim 1, wherein the inflatable port is one of molded, extruded and sewn.

* * * * *